United States Patent [19]
Doyle

[11] Patent Number: 6,048,480
[45] Date of Patent: Apr. 11, 2000

[54] ULTRA-HIGH MOLECULAR WEIGHT POLYETHYLENE

[75] Inventor: Christina Doyle, Cranleigh, United Kingdom

[73] Assignee: Howmedica International Inc., Ireland

[21] Appl. No.: 08/742,539

[22] Filed: Nov. 1, 1996

[30]     Foreign Application Priority Data

Nov. 2, 1995 [GB] United Kingdom .................. 9522477

[51] Int. Cl.⁷ .................................................. B29C 55/00
[52] U.S. Cl. ........................ 264/154; 264/155; 264/156; 264/138; 264/291; 264/292
[58] Field of Search .................................. 264/292, 291, 264/154, 155, 156, 138

[56]     References Cited

U.S. PATENT DOCUMENTS

| | | | |
|---|---|---|---|
| 4,587,163 | 5/1986 | Zachariades | 428/292 |
| 4,801,419 | 1/1989 | Ward | 264/292 |
| 5,026,511 | 6/1991 | Sano | 264/320 |
| 5,030,402 | 7/1991 | Zachariades | 264/138 |
| 5,234,652 | 8/1993 | Woodhams et al. | 264/210 |
| 5,290,498 | 3/1994 | Shiraki | 264/209.2 |

FOREIGN PATENT DOCUMENTS

| | | |
|---|---|---|
| 0157601A2 | 10/1985 | European Pat. Off. . |
| 0310449A2 | 4/1989 | European Pat. Off. . |
| 0371769A2 | 6/1990 | European Pat. Off. . |
| 0507613A2 | 10/1992 | European Pat. Off. . |
| 1480479 | 7/1977 | United Kingdom . |
| 2060469B | 9/1983 | United Kingdom . |
| 2156733B | 10/1987 | United Kingdom . |
| 2225551B | 2/1993 | United Kingdom . |

OTHER PUBLICATIONS

"The Production of oriented polymers by hydrostatic extrusion", by B. Parsons & I.M. Ward, in Plastics and Rubber Processing and Applications, 1982, pp. 215–224.

*Primary Examiner*—James Derrington
*Attorney, Agent, or Firm*—Lerner, David, Littenberg, Krumholz & Mentlik, LLP

[57]     ABSTRACT

A Process is described in which the polymer is passed over a former under hydro-static pressure, which may involve passing the material over a die or series of dies for the purpose of imposing multi-axial expansion to the workpiece. Some of the advantages are increased stiffness and reduction in creep. Improved wear is also found.

10 Claims, 8 Drawing Sheets

MECHANICAL PROPERTIES (BATCH 1) MEAN + SE

POLYMER PIN ON PLATE WEAR TESTS
MEAN WEAR FACTOR ± 1SE (n=15)

MEAN ± SE WEAR FACTOR
METAL PIN ON POLYMER PLATE

ULTRA-HIGH MOLECULAR WEIGHT POLYETHYLENE

BACKGROUND OF THE INVENTION

1. Field of the Invention

This invention relates to a method of improving the wear quality of ultra-high molecular weight polyethylene.

2. Description of the Prior Art

In a paper published in PLASTICS AND RUBBER PROCESSING AND APPLICATIONS II (1982)(215–224), "The Production of Orientated Polymers by Hydrostatic Extrusion" by B. Parsons and I. M. Ward, there is a discussion on small and large scale hydro-static extrusion experiments on a range of polymers with particular reference to polyethylene and polyoxymetholene. Hydro-static extrusion is shown to be a viable forming process for polymeric material and considerable property enhancement is said to be achieved. In this paper it is stated to be known that appreciable improvements in the stiffness of polymers can be produced by a high degree of plastic deformation, for example by stretching. There is reference to synthetic fibers, such as Nylon (polyamide) or polyethylene terethphthlate (polyester) being treated with a draw ratio (the ratio of final stretch length of the filaments to the initial length) which is comparatively small (typically about 5).

The paper goes on to state that it was considered that the draw ratio set a limitation to the degree of molecular alignment and corresponded to stretching the network of polymer molecules to some geometric limit—the "natural draw ratios"—after which fracture of the chains occurred.

A process is described in which the polymer is extruded into a tube shaped product under hydro-static pressure, which involves passing material over a fixed mandrel and a semi-conical plug for the purpose of imposing some hoop expansion to part of the billet material. There is reference to the extruded materials showing a marked improvement in thermal properties and other advantages. Some of the advantages are said to be increased stiffness, reduction in creep. Improved chemical resistance, low permeability to gases, high melting temperature, reduced shrinkage, very low axial expansion coefficient and high axial thermal conductivity are found, but it goes on to state that there may be possible defects, one of which is said to be deterioration in dry wear properties.

GB 2 060 469 relates to the deformation of thermoplastic polymers, to the solid phase deformation and concomitant orientations of orientatable thermoplastic polymers. There is reference to drawing an article through a die so as to induce a substantial degree of molecular orientation throughout the drawn article. There is also reference to a deformation ratio which is said to be the ratio of the cross-sectional area of the polymer billet to that of the extruder die orifice and in a discussion of U.K. Patent 1 480 479 there is reference to deformation ratios greater than about 8:1. GB 2 060 469 itself is related to a process for drawing the workpiece through the die so that its plastics strain is progressively increased during start up of the process. It is stated that the process produces a product with increased Young's modulus; resistance to creep; resistance to gas transport; enhanced deadfold; of axial thermal conductivity and it further states that the polymer should have a weight average molecular weight less than 1,000,000. The specification goes on to state that the die drawing process can be used as a forming process for polymers with higher molecular weight, but that this will not produce the enhanced properties listed.

In this specification, deformation ratio is used to define the ratio of the initial cross-sectional area of the workpiece to the final cross-sectional area of the product.

In the description of FIG. 1 it states that the polymer coating is drawn through a converging die and deformation of the polymer continues beyond the drawing block for some distance before it becomes frozen out. Thus, is this arrangement the molecular orientation is probably lengthwise in the produce or parallel to the draw direction. The advantages of the process are defined in all the examples by referring to the Young's modulus of the material achieved.

GB 2 156 733 relates to a process for solid phase deformation of tubular materials of an orientatable, thermoplastic polymer and to the orientated tubular material so produced.

This invention is intended to provide improved mechanical properties, especially in the directions other than the machine direction, that is the drawing direction, and there is reference to the drawing of a hollow workpiece through a die and simultaneously over an internally positioned former. Again, the specification states that when it is intended to produce a product with enhanced Young's modulus; resistance to creep; and resistance to gas transport; enhanced deadfold; or enhanced axial thermal conductivity, then the workpiece should desirably comprise a polymer having a weight average molecular weight of less than 1,000,000. As in the previously referred to G 2 060 469, the specification states that the process may be used as a forming process but not providing the enhanced properties listed above and it could, for example, be used with an ultra-high molecular weight polymer having a molecular weight of about 3,000, 000.

Very clear orientated polyester material is referred to using a nominal deformation ratio of at least 2:1 and preferably at least 3:1 and there is reference to the clarity of the workpiece.

GB 2 225 551 refers to a similar process for producing a biaxially oriented tubular material in which the deformation is carried out in the absence of any external force acting in a direction which is perpendicular to the axis of the workpiece. In this specification there is reference to hoop draw ratio which is defined as a ratio of the final hoop dimension to the initial hoop dimension, (i.e. measured circumferentially) and the axial draw ratio is the ratio of the initial bulk cross-sectional are of the hollow workpiece to the final bulk cross-sectional area of the product. The specification states that for polymeric polyethylene the inner hoop draw ratio is at least 1.2 and more preferably at least 1.5 and most preferably at least 2 and the preferred axial draw ratio is at least 2 and preferably greater than 3. It also states that the outer draw ratio may be less than 1 but is preferably at least 1 and more preferably at least 1.5 or 2 and the ratio of the axial draw ratio to the inner hoop draw ratio is preferably at least 1 and less than 4, most preferably less than 2. The specification also refers to the use of polyethylene polymers having a weight average molecular weight of from 50,000 to 150,000 and also to polymers above 300,000.

Ultra high molecular weight polyethylene is used as a bearing material for various applications, for example in the bearing surfaces of the joints in prostheses. Various orthopedic manufacturers have sought methods of improving the wear properties and reducing the amount of generated wear debris from the bearing surfaces of such joints. It has been the intention of these projects to explore "improved" polyethylenes especially those produced by post processing. A number of potential improvements have been seen in recent years on the market, some of which have already failed to fulfil clinical expectations, for example carbon reinforced polyethylene, and cross-linked polyethylene.

SUMMARY OF THE INVENTION

The present invention therefore relates to a method of improving the wear quality of ultra-high molecular weight polyethylene (UHMWPE) with a molecular weight greater than 1,000,000.

As will be seen from the discussion of the prior art, investigation has been directed to means for orientating thermoplastic polymers, but these have been basically directed to polymers with a weight average molecular weight less than 1,000,000 and it will also be seen that in the prior art it has been stated that although the die drawing process can be used as a forming process for polymers with high molecular weight this does not produce the enhanced properties which have been achieved with lower molecular wights and it has been stated that it was thought that the processes described do not enhance wear properties.

It has now been found by experiment that the wear properties of ultra-high molecular weight polyethylene can be improved by subjecting a workpiece to certain influences. According to the present invention a method of improving the wear quality of ultra-high molecular weight polyethylene with a molecular weight greater than 1,000,000 includes subjecting a workpiece to solid phase deformation in at least two directions to cause a preferred multi-axially orientation, said deformation in at lest tow directions, having a deformation ratio of 1.3 to 1.9. The preferred deformation ratios in each direction are 1.5 to 1.5.

The ultra-high molecular weight polyethylene preferably has a molecular weight greater than 4,000,000. The first deformation can be performed in a lengthwise direction of the workpiece and a second deformation performed in a substantially transverse direction thereto. The second deformation ratio can be greater than the first.

In a preferred method the workpiece is hollow and is passed over a former of increasing cross-sectional area, the second deformation taking place in a hoop direction. The hollow workpiece can be passed over the former without applying external force. In another method the workpiece is solid and can be square or of rectangular cross-section transverse to its length.

In another method the workpiece can be drawn through a die and/or over a former. Alternatively the workpiece can be pressed through the die and/or over the former.

The invention also includes a UHMWPE workpiece which has been treated by the method set forth above.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

The present invention is focused on biaxial orientation of ultra high molecular weight polyethylene to enhance its properties in at least two directions, and establishes conditions, where the strain energy to failure of the modified material is maintained and the proof or yield stress of the material is increased.

Figure 1:
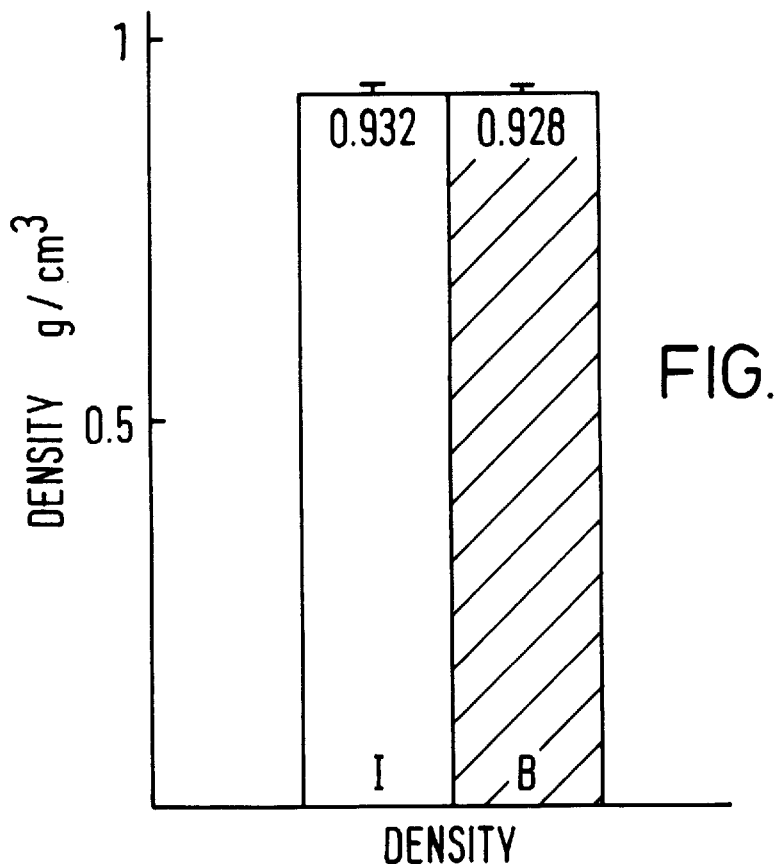
FIG. 1 is a graph showing the relative density of drawn materials (B) according to the present invention relative to drawn isotropic source material (I)
Figure 2:
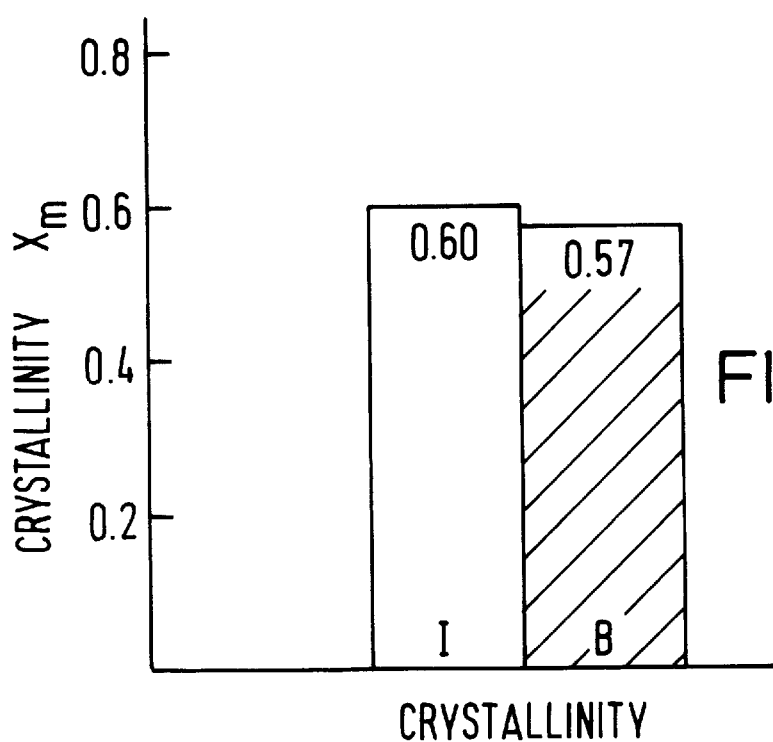
FIG. 2 is a graph showing the relative crystallinity of the material (B) made according to the invention relative to isotropic source material (I)

The invention demonstrates for the first time successful die drawing of GUR412 (MW 4.5 million) UHMWPE in both uniaxial and biaxial forms. The drawn materials had similar density and crystallinity as shown in FIGS. 1 and 2 to the isotropic source material. The molecular orientation of the drawn material was confirmed by X-ray diffraction.

The material was intended for use as polymer components in artificial joint which undergo complex loading regimes, stress field and wear patterns, it was considered preferably to enhance the properties of the UHMWPE in two directions, by using biaxial drawing methods.

Figure 3:
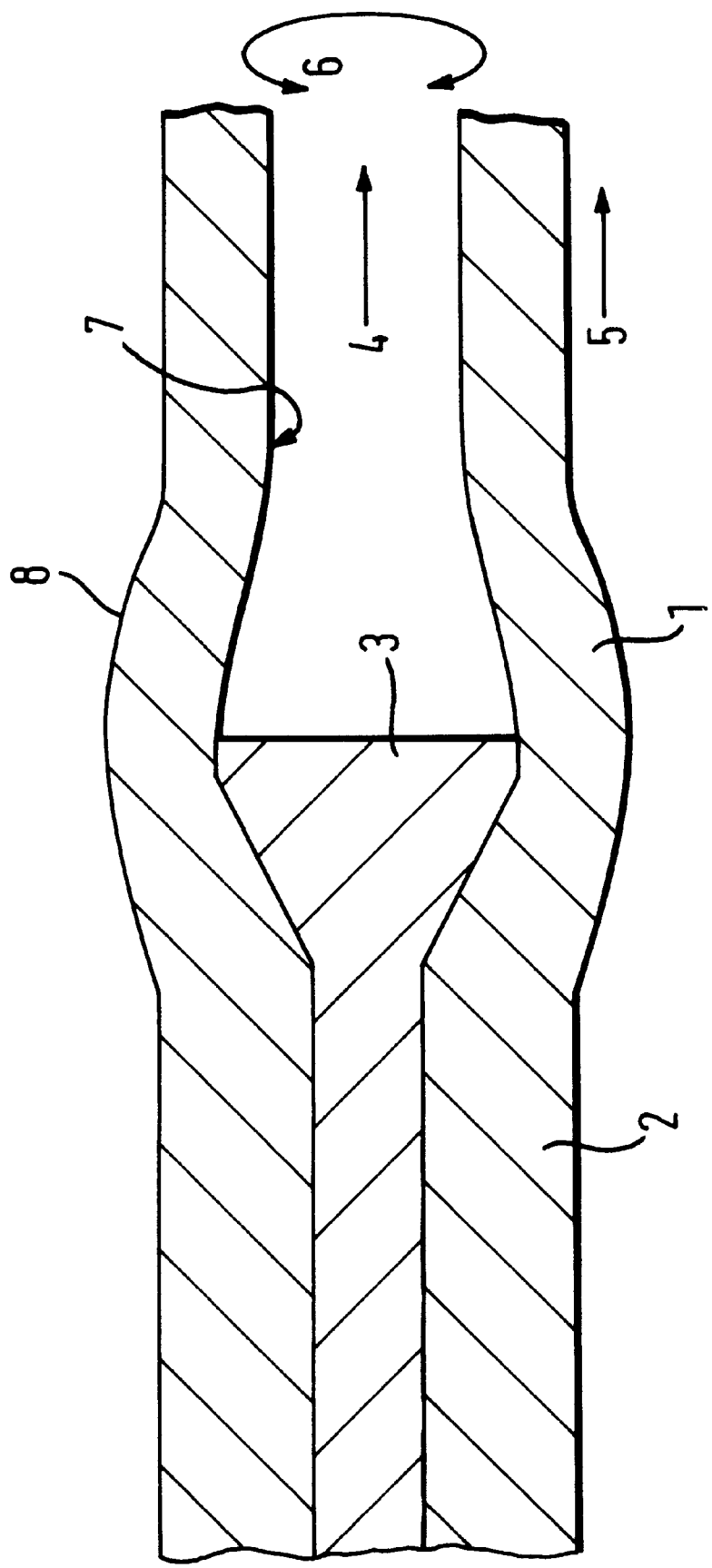
FIG. 3 is a diagrammatic representation of the method used according to one aspect of the present invention.
Figure 4:
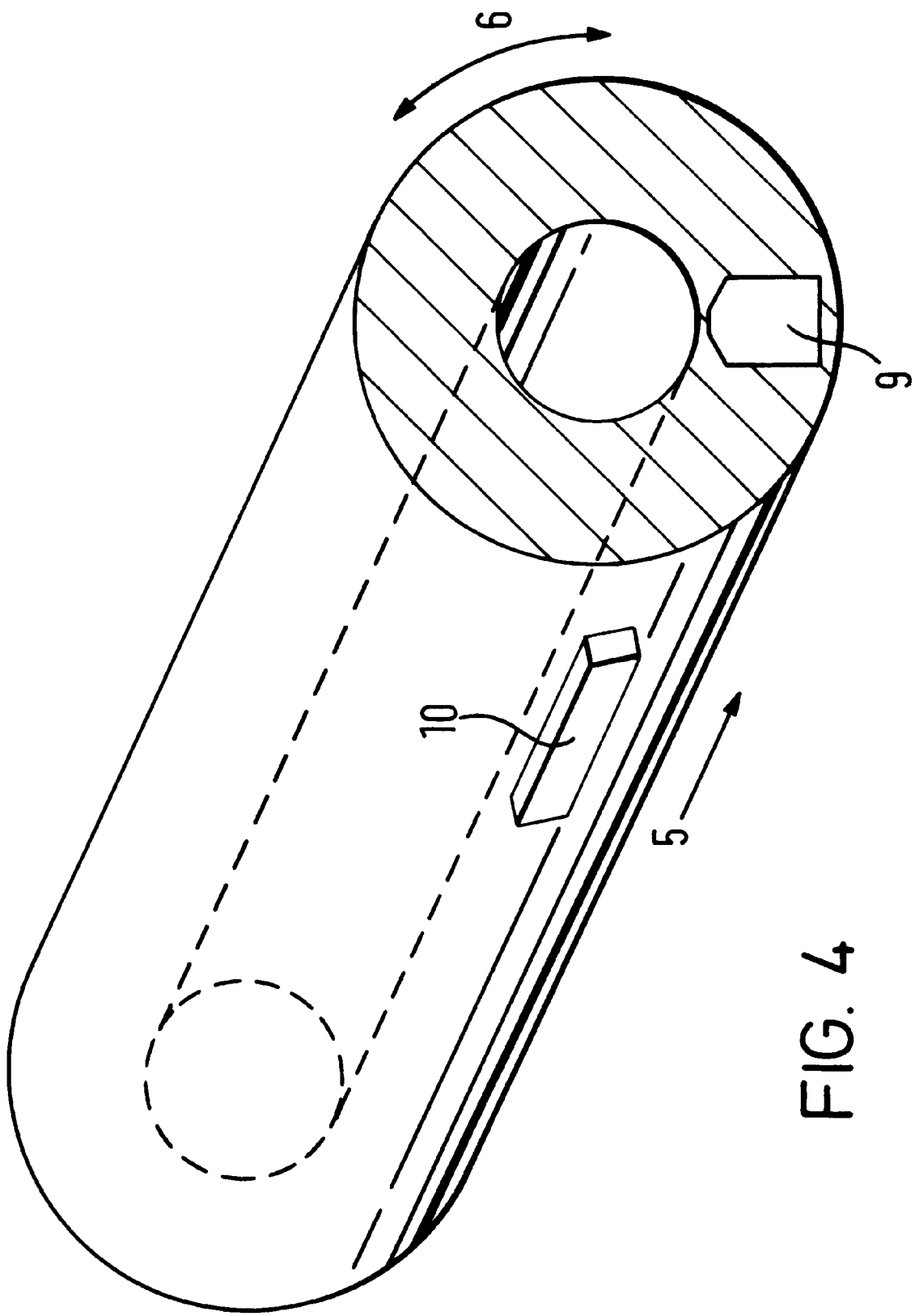
FIG. 4 is a diagrammatic perspective view of a material produced according to the invention.

FIG. 3 shows a method used for biaxial orientation of a thick walled tube 1, by drawing a material 2 over a mandrel 3 which is of increasing diameter over its length in the direction of draw indicated by reference numeral 4. Such a method of drawing polyethylene material to produce solid phase deformation is described in GB 2 225 551, but the effects produced by the present invention were unexpected considering the information set out, for example in the prior art documents referred to above. This method produced orientation in both the longitudinal direction indicated by arrow 5 and hoop direction indicated by arrow 6, as shown in FIGS. 3 and 4, with a higher draw deformation ratio and orientation near the internal surface of the tube 7 than the outside 8 in the hoop direction 5.

Material was produced such that the draw ratios close to the internal surface 7 were similar in magnitude in both the hoop 6 and longitudinal direction 5.

Figure 5:
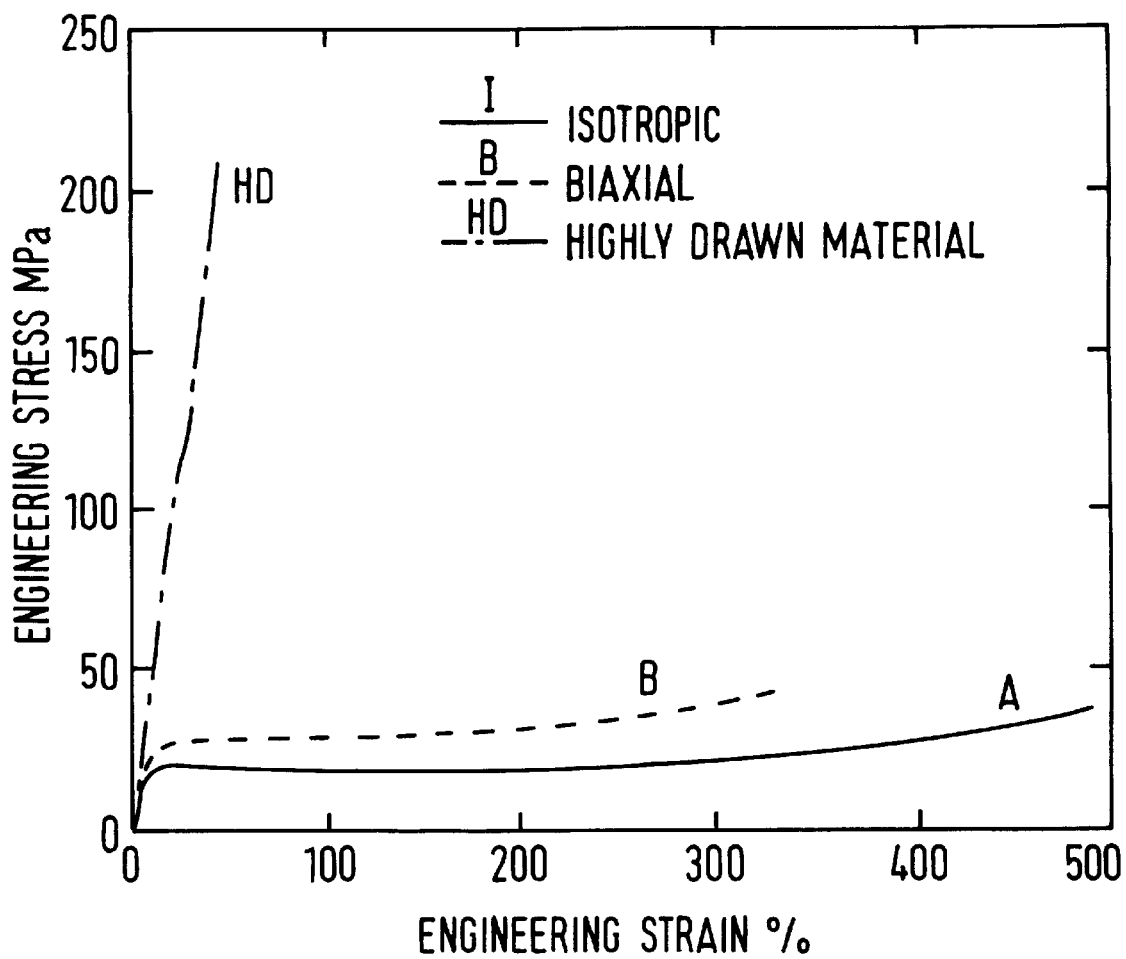
FIG. 5 is a graph showing typical engineering stress strain curves.
Figure 6:
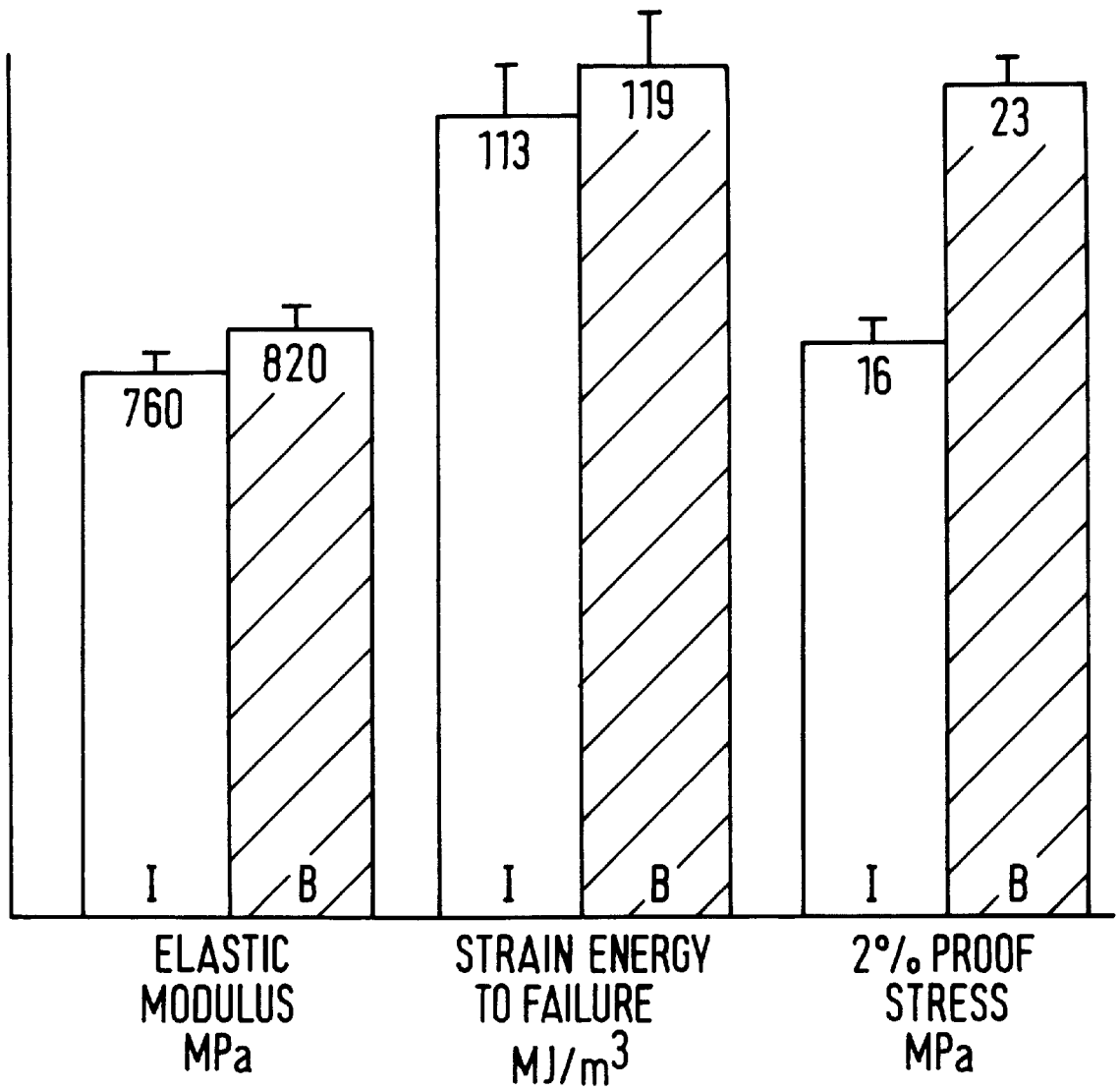
FIG. 6 is a graph showing strain energy to failure and elastic modulus of material made according to the invention in comparison with isotropic materials.
Figure 7:
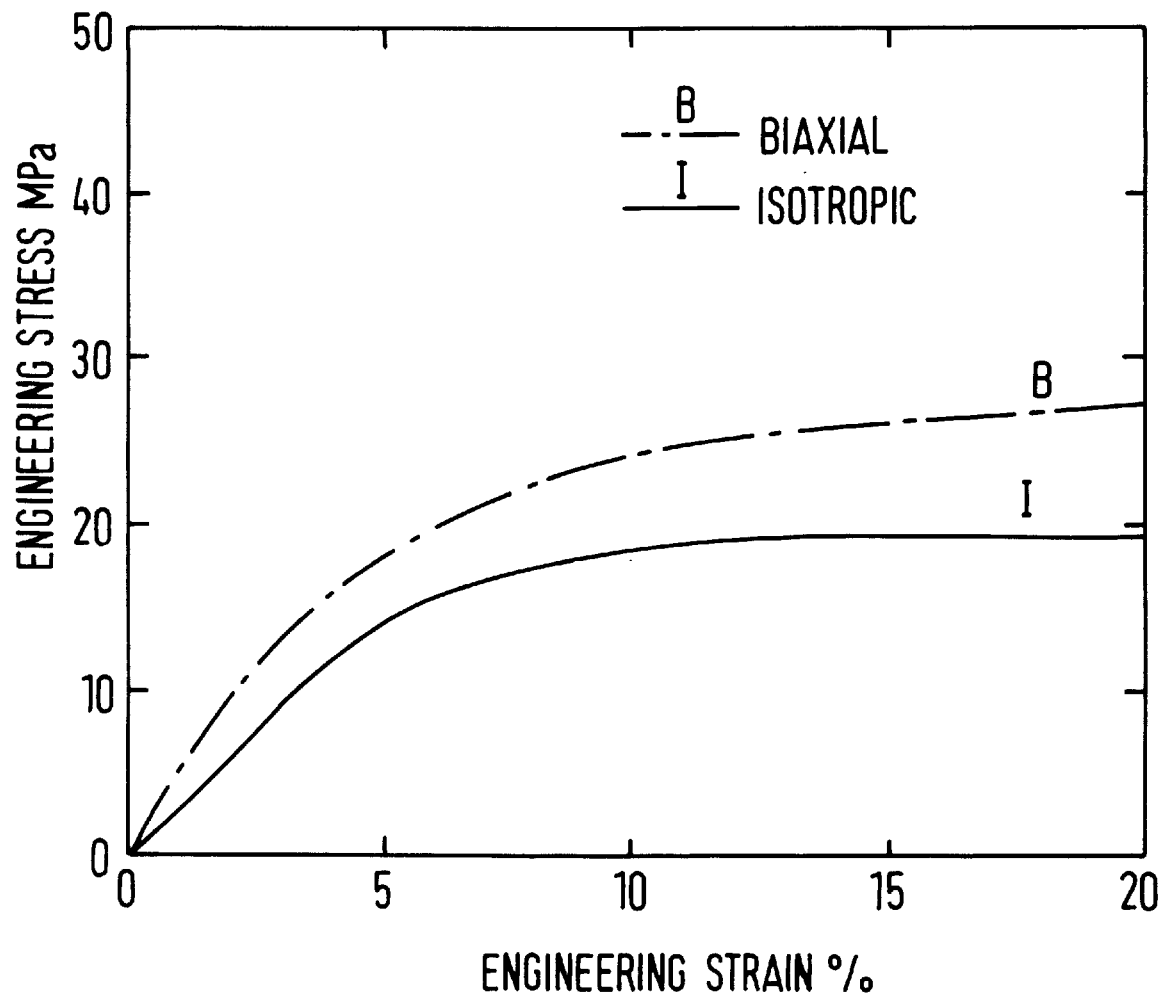
FIG. 7 is a graph showing stress strain curves for materials made according to the invention relative to isotropic materials.

FIG. 5 shows typical engineering stress strain curves taken in tension in the longitudinal direction for the isotropic or standard material (A) and biaxially orientated material (B) with a draw ratio of 1.5 in each direction. This shows that the drawn material had a reduction in the strain to failure, approximately similar strain energy to failure and a higher proof stress and working stress range compared to the isotropic material. Increasing the draw ratio further adversely affected both the strain and strain energy to failure, producing a much more brittle material as shown in the curve for the highly drawn uniaxial material with a ratio of 4 to 1 as shown in FIG. 5. Biaxially drawn material with a draw ratio of approximately 1.5 in each direction was considered to produce the most appropriate change in properties with a statistically significant increase in proof stress and working stress range while maintaining a similar strain energy to failure and elastic modulus to the isotropic material as shown in FIG. 6. A detailed examination of the stress strain curve for the two materials sat low strains shows clearly the improved characteristics of the biaxially oriented material as shown in FIG. 7.

Seven one meter long lengths of thick walled tube were produced from three different 75 mm thick slabs of UHMWPE. The final dimensions of the drawn tube produced a wall thickness of between 10 and 15 mm with an outside diameter of 63 mm. The drawn material was found to have some dimensional instability when machined components were taken from the drawn tube, due to the release of inbuilt strains.

Two types of wear tests were carried out, a polymer pin on a metal plate with reciprocating motion, and a spherical ended metal pin on polymer plate under reciprocating motion. The first test configuration may be considered more appropriate for hip joint applications, while the second test may be considered more suited to knee joint applications. The polymer pins and plates were taken with their wear surfaces close to the internal diameter of the drawn tube, where the draw ratio was approximately 1.5 in each direction, such a pin 9 and a plate 10 are shown in FIG. 4. Each test consisted of a direct comparison between the biaxial material and the isotropic control material. Tests were carried out for sliding distances greater than 250 km (greater than 10 years equivalent), with more than 15 measurements in each test to allow statistical analysis. Tests were run in bovine serum as a lubricant, and the wear rate was expressed as a normalized wear factor K when, $$\text{Wear Factor} = \frac{\text{Wear Volume}}{\text{Load and Sliding Distance}}$$

Figure 8:
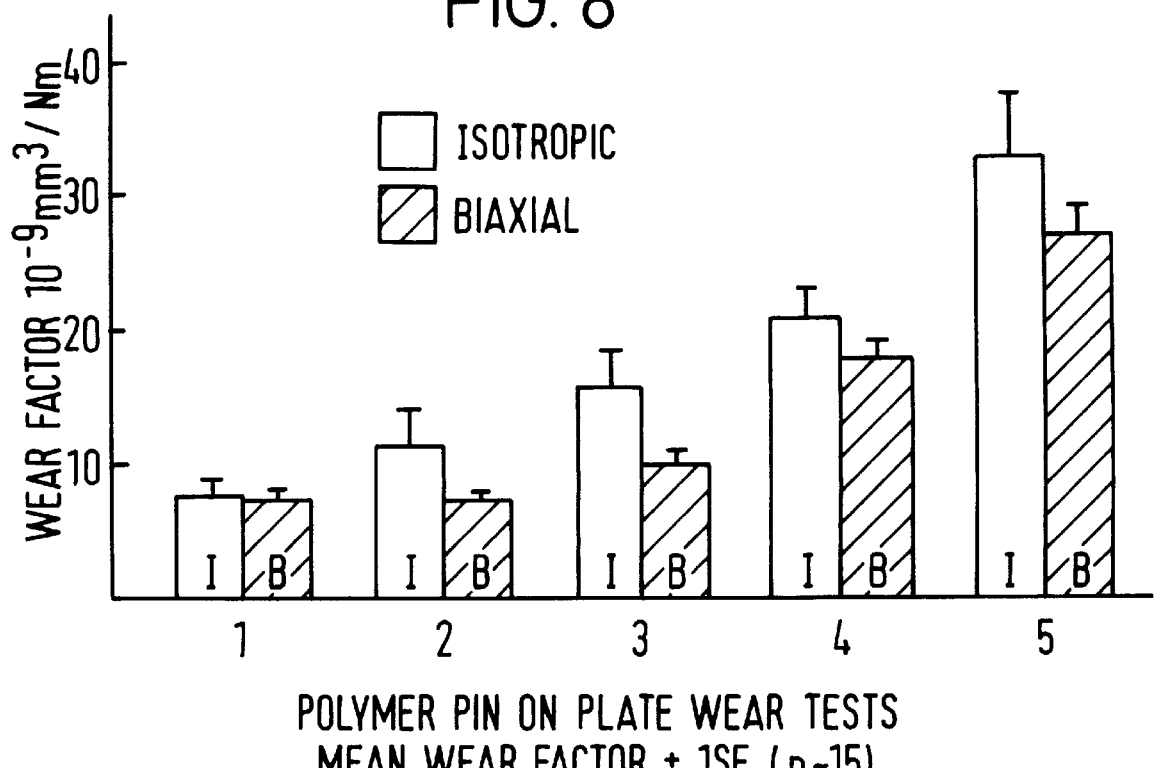
FIG. 8 is a graph showing wear test results.

The results of five sets of polymer pin 9 on plate tests are shown in FIG. 8. or each of the tests are set out below.

| Polymer Pin on Plate Wear Tests | |
|---|---|
| 1 | 200 N Load |
| 2 | 160 N Load |
| 3 | 160 N Load |
| 4 | 80 N Load |
| 5 | 80 N Load (rough counterface) |

In each of the tests the biaxial material has a lower wear rate than the isotropic the control material. The diffferences were statistically significant at the 20% level in Tests 2 and 3. Overall, the wear factor for the biaxial material was reduced by 22% compared to the isotropic material.

Figure 9:
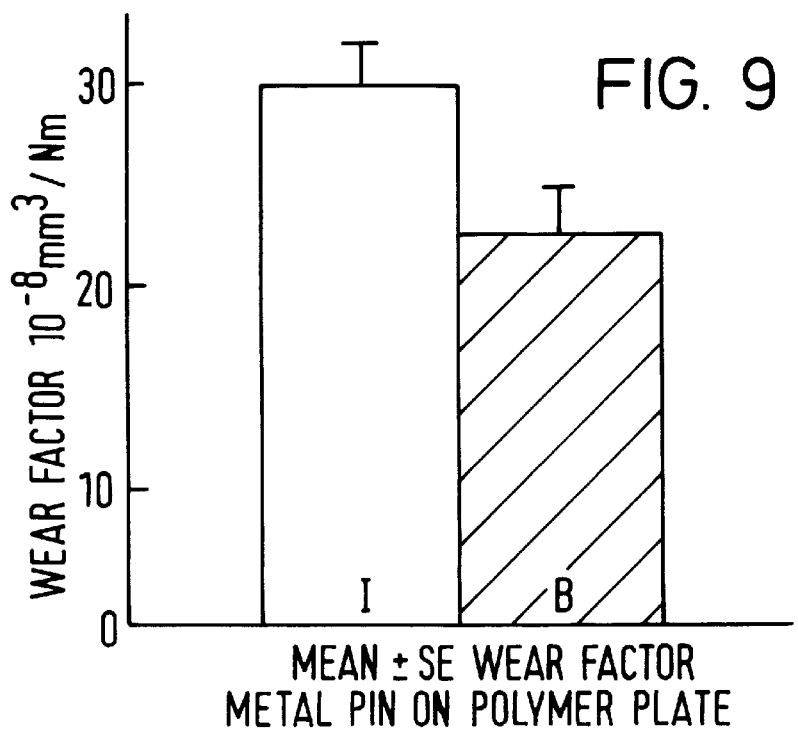
FIG. 9 is another graph showing wear test results.

The results for the polymer plate 10 on a pin test are shown in FIG. 9. The isotropic material showed a higher wear factor than the biaxial material and this was statistically significant at the 5% level. The biaxial drawing of the material was predicted to produce a 25% reduction in the wear rate of this test.

Figure 10:
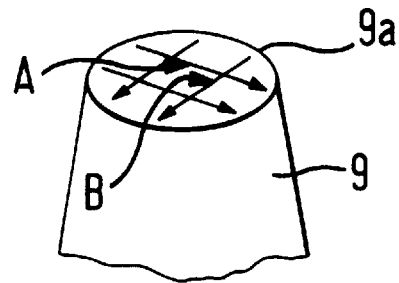
FIG. 10 is a diagrammatic view of a pin used for testing.
Figure 11:
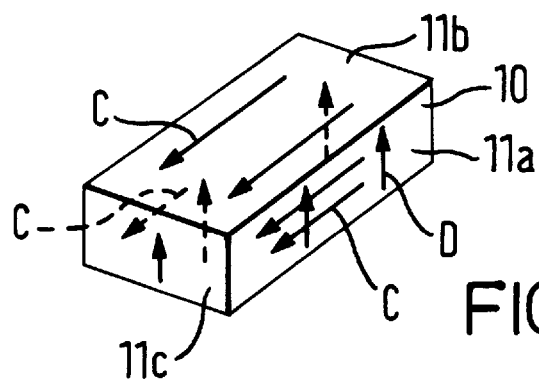
FIG. 11 is a diagrammatic view of a plate used for testing.

FIGS. 10 and 11 are intended to illustrate what is thought to be the lines of molecular orientation on the test pieces. Thus, FIG. 10 shows the work surface 9a on the ind of the pin 9. The general direction of the molecular orientation is shown to be in two directions by arrows A and B. The point from which the pin has been taken is shown in FIG. 4 and it will be seen that the lines of orientation are substantially at right angles to each other across the surface.

In FIG. 11 the lines of orientation are again shown in two directions C and D on one face 11a of the plate 10. It will be seen that the lines of orientation are at right angles on this face. On the face 11b however, although the lines of orientation C and D are again at right handles, the lines D exhibit their ends towards the face and on the face 11c the lines of orientation D extend across the face, but the lines C again exhibit there ends.

It will be appreciated that the above figures only show assumed lines of orientation and are meant to be interpreted in general terms.

From the experimental results set forth above, it is assumed that the best wear qualities are obtained when the lines are at right angles across the face, as shown in FIG. 10, although this assumption may be only the result of the two different types of experiments applied.

As will be seen from the above, the mechanical properties of ultra high molecular weight polyethylene have been enhanced by biaxial drawing and a significant increase in proof stress and working stress range has been achieved, while maintaining the strain energy to failure.

Wear tests have shown that this can produce a 22 to 25% reduction in the wear rate of the biaxially drawn materials compared to the isotropic UHMWPE.

Figure 12:
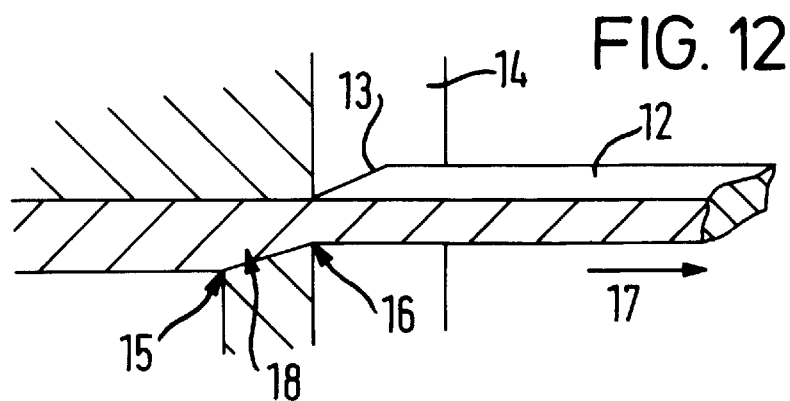
FIG. 12 is a diagrammatic perspective view of another method according to the invention.

An alternative method of causing solid phase deformation in at least two directions to ultra high molecular weight polyethylene (UHMWPE) can be applied by a slot type drawing method. As shown in FIG. 12, a rectangular or square strip of pre-machined UHMWPE 12 is drawn through a slot 13 of a slot-type die 14 having an entry opening 15 and a discharge opening 16. The direction of draw is indicated by arrow 17 and the transverse width of the slot 13 is equivalent to the transverse width of the strip 12 at entry.

With this arrangement there is solid phase deformation in the draw direction 17 and at an angle thereto, indicated by arrow 18 in the die slot, thus causing solid phase deformation in two directions to cause the preferred multi-axial orientation.

The deformation ratios, that is the draw ratio and in effect the compression ratio in the slot, are both between 1.3 to 1.9.

Figure 13:
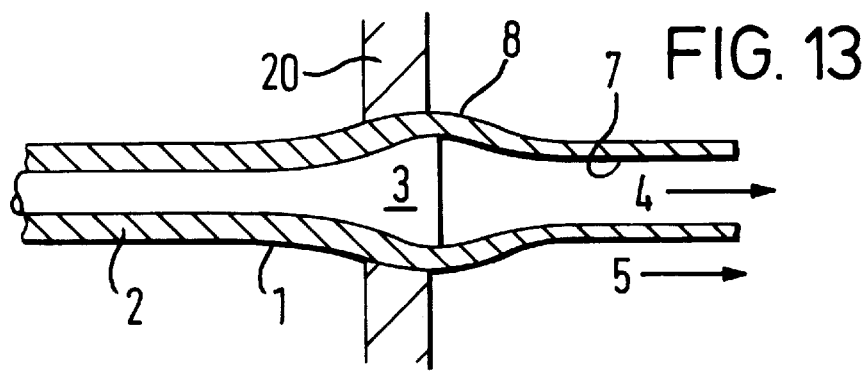
FIG. 13 is a diagrammatic side elevation of a third method of applying the invention.

FIG. 13 shows a method similar to that described and shown in FIG. 3 and the same reference numerals are used to indicate similar parts but in this method the tube of material also passes through a control die 20.

Other methods of producing solid phase deformation in at least two directions will be apparent to those skilled in the art, for example rolling and drawing, the governing factor being that the deformation ratios are between 1.3 to 1.9to produce the preferred multi-axial orientation.

In the method described with regard to FIGS. 1 to 9 the material produced is described as being intended for bearing elements in prosthetic joints, but it will be appreciated that there are many other applications for the material produced.

I claim:

1. A method of preparing components having improved wear quality of a wear surface made of ultra-high molecular weight polyethylene with molecular weight greater than 1,000,000 comprising subjecting a workpiece to solid phase deformation in at least the longitudinal direction and the hoop direction by forming a tube by passing the polyethylene workpiece over a mandrel of increasing diameter over its length to cause orientation of polyethylene chains in said two directions, said deformation in said two directions, having a deformation ratio of 1.3 to 1.9 and taking the wear surface from close to the internal diameter of the formed tube by machining components from the tube.

2. The method as claimed in claim 1 wherein said deformation ratios in each direction are 1.5 to 1.6.

3. The method as claimed in claim 2 wherein the ultra-high molecular weight polyethylene has a molecular weight greater than 4,000,000.

4. The method as claimed in claim 1 wherein the first deformation is performed in a lengthwise direction of the workpiece and a second deformation is performed in a hoop direction which is a substantially transverse direction thereto.

5. The method as claimed in claim 4 wherein the second deformation ratio is greater than the first.

6. The method as claimed in claim 5 wherein the workpiece is hollow and passed over a former of increasing cross-sectional area, the second deformation taking place in a hoop direction.

7. The method as claimed in claim 5 wherein the workpiece is solid.

8. The method as claimed in claim 7 wherein the workpiece has a square or rectangular cross-section in a direction transverse to its length.

9. The method as claimed in claim 8 wherein the former is a die and said workpiece is drawn therethrough.

10. A method as claimed in claim 8 wherein the workpiece is forced over a forming die.

* * * * *

UNITED STATES PATENT AND TRADEMARK OFFICE
CERTIFICATE OF CORRECTION

PATENT NO. : 6,048,480
DATED : April 11, 2000
INVENTOR(S) : Doyle

It is certified that error appears in the above-identified patent and that said Letters Patent is hereby corrected as shown below:

On title page item [57],
    line 1, "Process" should read -- process --.

Column 2, line 4, "is" should read -- in --.
Column 2, line 42, "are" should read -- area --.
Column 3, line 15, "wights" should read -- weights -- .
Column 3, line 26, "lest tow" should read -- least two --.
Column 3, line 28, "1.5" (second occurrence) should read -- 1.6 --.
Column 4, line 36, after "patterns", insert -- ; --.
Column 5, line 8, "sat" should read -- at --.
Column 5, line 42, cancel the word "or".
Column 5, line 42, after "8.", insert -- The specific conditions for --.
Column 5, line 55, cancel the word "the" (second occurrence).
Column 5, line 67, "ind" should read -- end --.
Column 6, line 13, "there" should read -- their --.
Column 6, line 56, insert a space between "1.9" and "to".

Signed and Sealed this

Third Day of April, 2001

*Attest:*

NICHOLAS P. GODICI

*Attesting Officer*     *Acting Director of the United States Patent and Trademark Office*